(12) United States Patent
Ohana Lubelchick

(10) Patent No.: US 10,376,197 B2
(45) Date of Patent: Aug. 13, 2019

(54) DIAGNOSING SYSTEM FOR CONSCIOUSNESS LEVEL MEASUREMENT AND METHOD THEREOF

(71) Applicant: Penina Ohana Lubelchick, Tel Aviv-Jaffa (IL)

(72) Inventor: Penina Ohana Lubelchick, Tel Aviv-Jaffa (IL)

( * ) Notice: Subject to any disclaimer, the term of this patent is extended or adjusted under 35 U.S.C. 154(b) by 0 days.

(21) Appl. No.: 15/152,485

(22) Filed: May 11, 2016

(65) Prior Publication Data

US 2016/0249842 A1  Sep. 1, 2016

Related U.S. Application Data

(63) Continuation-in-part of application No. 13/820,949, filed as application No. PCT/IL2011/000704 on Sep. 5, 2011, now abandoned.

(30) Foreign Application Priority Data

Sep. 7, 2010 (IL) .......................................... 208055

(51) Int. Cl.
*A61B 5/16* (2006.01)
*A61B 5/00* (2006.01)
(Continued)

(52) U.S. Cl.
CPC ............ *A61B 5/167* (2013.01); *A61B 5/0022* (2013.01); *A61B 5/165* (2013.01); *A61B 5/4803* (2013.01);
(Continued)

(58) Field of Classification Search
None
See application file for complete search history.

(56) References Cited

U.S. PATENT DOCUMENTS 6,151,571 A * 11/2000 Pertrushin ............... G10L 17/26
704/207
6,159,015 A   12/2000 Buffington et al.
(Continued)

OTHER PUBLICATIONS

European Search Report for related EP Appln. No. 11823152.1, dated Mar. 17, 2016.
(Continued)

*Primary Examiner* — Bruk A Gebremichael

(57) ABSTRACT

The present invention relates to a method for detecting a personality consciousness code of an individual, comprising: a) storing reference voice characteristics of different persons that represent acoustic information as expressed by human voice in a form of a time to frequency component relation; b) classifying the acoustic information into 12 different personality consciousness codes by using support vector machine that analyzes said acoustic information; c) receiving data indicative of a sound energy generated by the voice of said individual; d) performing spectral analysis of said received sound energy in order to obtain voice characteristics from an electronic representation of said sound energy; and e) comparing said obtained voice characteristics with the reference voice characteristics and determining the personality consciousness code of said individual by using the support vector machines, and using the obtained voice characteristics to determine the level of consciousness.

18 Claims, 10 Drawing Sheets

(51) Int. Cl.
  *G10L 25/18* (2013.01)
  *G10L 25/63* (2013.01)
  *G10L 25/66* (2013.01)

(52) U.S. Cl.
  CPC ............ *A61B 5/7278* (2013.01); *G10L 25/18* (2013.01); *G10L 25/63* (2013.01); *G10L 25/66* (2013.01); *A61B 5/7246* (2013.01); *A61B 5/7264* (2013.01)

(56) References Cited

U.S. PATENT DOCUMENTS

| | | |
|---|---|---|
| 2002/0010587 A1 | 1/2002 | Pertrushin |
| 2004/0243443 A1 | 12/2004 | Maskazu et al. |
| 2006/0073451 A1* | 4/2006 | Thornley ................ G09B 7/02 434/236 |
| 2007/0154876 A1 | 7/2007 | Harrison, Jr. |
| 2007/0250349 A1 | 10/2007 | Tieger et al. |
| 2007/0288406 A1 | 12/2007 | Visel |
| 2009/0103709 A1 | 4/2009 | Conway et al. |
| 2009/0210281 A1 | 8/2009 | Baldwin et al. |
| 2009/0295088 A1 | 12/2009 | Chan |
| 2009/0319338 A1 | 12/2009 | Parks |
| 2010/0106044 A1 | 4/2010 | Linderman |
| 2010/0198760 A1 | 8/2010 | Maddage et al. |
| 2013/0172693 A1 | 7/2013 | Lubelchick |
| 2014/0372080 A1 | 12/2014 | Chu |

OTHER PUBLICATIONS

Hawkins, D., Power versus Force: The Hidden Determinants of Human Behaviour, 2002, pp. 45, 50-53, 60-63, 95-96.

Srikanth, N. et al., Behavioral Signal Processing Deriving Human Behavioral Informatics from Speech and Language, Proc IEEE Inst Electr Electron Eng., Feb. 7, 2013, 101(5), pp. 1203-1233.

Schuller, B. et al., A Survey on Perceived Speaker Traits: Personality, Likability, Pathology, and the First Challenge, Computer Speech and Language, (2015), 29(1), pp. 100-131.

Written Opinion, dated Aug. 13, 2017, for PCT/IL2017/050508.

* cited by examiner

| State | Scale | Level |
|---|---|---|
| Force | 50 | Depression |
| | 75 | Sadness |
| | 100 | Fear |
| | 125 | Lust |
| | 150 | Anger |
| | 175 | Egotism |
| Power | 200 | Courage |
| | 250 | Belief |
| | 300 | Positive |
| | 350 | Harmony |
| | 400 | Wisdom |
| | 500 | Love |
| | 550 | Inner peace |
| | 600 | Revelation |
| | 700-1000 | Supper consciousness |

Fig. 1

DIAGNOSING SYSTEM FOR CONSCIOUSNESS LEVEL MEASUREMENT AND METHOD THEREOF

CROSS-REFERENCE TO RELATED APPLICATIONS

This application is a continuation-in-part of U.S. application Ser. No. 13/820,949 filed Mar. 5, 2013, which is a U.S. National Stage of PCT/IL11/00704 filed Sep. 5, 2011, which in turn claims priority to Israeli Application No. 208055 filed Sep. 7, 2010, the contents of all of the foregoing applications being incorporated herein by reference in their entireties.

FIELD OF THE INVENTION

The present invention relates to the field of personality diagnosing system. More particularly, the invention relates to a Bio-Neuro Acoustic (BINA) platform which measures human consciousness and detects a personality consciousness code of an individual, and thereby enables to provide diagnosis, treatment or better decision making for a user based on a personal consciousness code.

BACKGROUND OF THE INVENTION

Consciousness is variously defined as subjective experience, or awareness, or wakefulness, or the executive control system of the mind. Some theorists—most of whom are physicists—have argued that classical physics is intrinsically incapable of explaining the holistic aspects of consciousness, but that quantum theory provides the missing ingredients. The most notable theories falling into this category include the Orch-OR theory formulated by Stuart Hameroff and Roger Penrose. Some of these quantum theories offer descriptions of phenomenal consciousness, as well as quantum interpretations of access consciousness.

The consciousness level of living organism is usually divided into four main levels: The first level is known as the instinctive level of consciousness, and it is defined as the lowest level of consciousness (mostly animals). The next level, the second level, is known as the emotional level. The third level is known as the logical thinking level where most of the people usually positioned, and the fourth level, the highest level, is known as the quantum thinking level. The ability to move up from the third level to the fourth level results in a change in the level of consciousness from a state of force to a state of power.

Dr. Valerie V. Hunt published a book "Infinite Mind: The Science of Human Vibrations of Consciousness", which elucidates an energy field that permeates the body. Using Kirlian and enhanced computer photography, as well as new instrumentation to record the human energy field as vibrations (i.e., frequencies), Dr. Hunt's work goes well beyond current mind-body theories. In her continuing research into consciousness, Dr. Hunt explains that the goal is not to give you emotional peace and relaxation, or follow any particular philosophy, but to access the mind field, not the brain, in order to view everyday problems from a higher level of consciousness. This can be done as scientists who have redefined the mind have discovered vibratory frequency patterns that coexist with patterns of consciousness.

The Human Energy Field & Consciousness (as documented in the Bioenergy Research Laboratory at UCLA) discloses that the atomic electrical energy of the cells becomes the auric field. The field is both inside and outside of the body where it colors all sensory information that must pass through the field and skin before it gets to the sensory nerve endings. Because the field has a corona on the outside of the body it is in direct contact with all the energies of the environment, living, mineral, and celestial. This is the primary way humans interact with the world. The human field is a dynamic ever-changing series of patterns of frequencies that oscillate up to one million cycles per second making it the fastest and most elaborate of the body's electrical systems. Each person has a unique signature pattern of frequencies, his base reference, to which he returns when his field is not stimulated. This is a base reference from which his field responds to other fields. The mind-field is the highest level of memory, containing information about the physical body, thoughts, feeling states and past and present life experiences, particularly if memory is of profound experiences. Emotions connected with higher states of consciousness organize the mind-field and make it susceptible to new and threatening situations. This level of emotion is the deepest motivation of behavior.

Psychiatrist and consciousness researcher Dr. David R. Hawkins developed a "map" of the levels of human consciousness (also called the Scale of Consciousness) that uses a muscle-testing technique called Applied Kinesiology (AK) to document the nonlinear, spiritual realm. According to Hawkins, humans live at vastly different "levels" of consciousness. All these levels, along with the "truth level" of ANY true/false style inquiry, can be tested for truth and numerically "calibrated" through muscle testing, on a logarithmic scale of 1-1000. According to Hawkins, any person, concept, thought or object that calibrates at 200 (The level of Integrity) or above is positive ("power"); anything below 200 is negative ("force").

According to Hawkins, the energy of a human thought is nonetheless absolutely measurable. A thought that emanates from the 100 level of consciousness will typically measure between $\log 10^{-800 \ million}$ to $\log 10^{-700 \ million}$ microwatts. On the other hand, a loving thought at the consciousness level of 500 measures approximately $\log 10^{-35 \ million}$ microwatts.

Briefly, each level of consciousness (LOC) coincides with determinable human behaviors and perceptions about life. Each level represents a corresponding attractor field of varying strength that exists beyond our three-dimensional reality. There's a critical point within each LOC from which its field gravitates (or entrains).

The numbers on the scale represent logarithmic calibrations (measurable vibratory frequencies on a scale which increases to the tenth power) of the levels of human consciousness and its corresponding level of reality. The numbers themselves are arbitrary; the significance lies in the relationship of one number (or level) to another. In the book "Power vs. Force: The Hidden Determinants of Human Behavior" by Dr. David R. Hawkins, there's an example for a hierarchy of levels of human consciousness (see FIG. 1). From low to high, the levels of consciousness are: shame, guilt, apathy, grief, fear, desire, anger, pride, courage, neutrality, willingness, acceptance, reason, love, joy, peace, enlightenment (e.g., Dr. Hawkins' scale is from 1 to 1000; a similar scale could be devised from 1 to 10 where 2 is courage and 5 is love).

While one can pop in and out of different levels at various times, usually there's a predominant "normal" state for each individual person. Hawkins defines these levels as a logarithmic scale, so there are far fewer people at the higher levels than at the lower ones. An increase from one level to another will result in enormous change in a person life. People can be ranked at these levels. Usually, within most people life, some parts of the life can be at different levels than others, but a person should be able to identify the current overall level.

According to the aforementioned researches and theories the level of consciousness can be defined as a range of frequencies, wherein each level is represented by specific frequency. Wherein, the higher the level of consciousness the higher is the frequencies. The value of each frequency is represented according to a logarithmic scale, thus the differences between adjacent frequencies values on the scale are relatively very high.

Progressing from one level to the next requires an enormous amount of energy. Personal growth experiences often occur in the form of a quantum leap—a strong and radical shift from one mindset to another. Without conscious effort or the help of others, many people likely just stay at their current level until some outside force comes into their life.

Going up even one level can be extremely hard; most people don't do so in their entire lives. A change in just one level can radically alter everything in someone's life. For example, people below the level of courage aren't likely to progress without external help. But, when someone hit the level of courage, all the past fears and false pride seems irrelevant.

In addition, today, most decisions of the people who need to make decisions, are results of job tests, human resources filtering, and other entities who need to define the personality type of a subject, all these are usually using techniques that are based on the subjective feedback from the subject, such as the answers of the subject to an introduced and predetermined set of questions. However, such techniques are very limited as they don't have the ability to provide an objective feedback from the subject. Moreover, although each person has a consciousness genetic code that affects his or her decisions, most people are not aware of it and how it affects them, thereby creating barriers to success.

Therefore, it is an object of the present invention to provide a system which is capable of obtaining a better decision making for a person based on a personal level of consciousness.

It is another object of the present invention to provide a system and method for aiding a person to improve the individual level of consciousness.

It is yet another object of the present invention to provide a system for detecting the personality code of a person.

It is still another object of the present invention to provide a system for providing recommendations to a person according to its personality code.

It is a further object of the present invention to provide learning and diagnosing system for consciousness level which enables to provide immediate treatment in real-time to a subject according to the subject's progress while using the system.

Other objects and advantages of the invention will become apparent as the description proceeds.

SUMMARY OF THE INVENTION

The present invention relates to a method for detecting a personality consciousness code of an individual, comprising: a) storing, in a database, reference voice characteristics of different persons that represent acoustic information as expressed by human voice in a form of a time to frequency component relation, wherein said acoustic information indicative of dominant elements, three energy routes and extraversion-introversion personality traits; b) classifying the acoustic information into 12 different personality consciousness codes, based on the determination that each personality code includes a dominant element, a balancing element, a transformational element, an energy route and a personality trait, by using support vector machine that analyzes said acoustic information; c) receiving, by a computing system, data indicative of a sound energy generated by the voice of said individual; d) performing, by the computing system, spectral analysis of said received sound energy in order to obtain voice characteristics from an electronic representation of said sound energy in the form of a time to frequency component relation, wherein said analysis detects the characteristics that defines the personality consciousness code; and e) comparing said obtained voice characteristics with the reference voice characteristics and determining the personality consciousness code of said individual by using the support vector machines, and using the obtained voice characteristics to determine the level of consciousness (LOC).

According to an embodiment of the invention, the spectral analysis includes octaves analysis for detecting the coherent between the 12 notes at each octave, wherein the coherent level between the notes reflects the level of balance of the personality consciousness code, so that fulfilling of missing notes allowing the individual to move up from the current LOC to a higher LOC.

According to an embodiment of the invention, the dominant element is determined by applying spectral analysis to the sound energy generated by the individual voice, in order to extract speech intensity, speech pace, tone recognition and the coherent between the 12 notes on an octave scale.

According to an embodiment of the invention, the energy route is determined by dividing the captured sound energy into time units and summing the appearance of each specific tone on an octave scale, wherein the octave scale includes 8 octaves and each octave includes 12 notes, so that each group of 4 notes in an octave defines a different energy route, a dynamic energy (d), a permanent energy (pr) and a non-permanent energy (n), wherein the energy route is determined in a group of notes where the tones value have the highest values and that these values are similar.

According to an embodiment of the invention, the extraversion-introversion personality trait is determined by applying spectral analysis to the sound energy generated by the individual voice, in order to extract pitch levels and speech mobility, where high values of pitch and speech mobility indicates extroverted personality and low values of pitch and speech mobility indicates introverted personality.

According to an embodiment of the invention, the personality code includes a dominant element, a balancing element and a transformational element, wherein the relations between said elements is such that a relatively slight change in the transformational element will result in the largest change in the dominant and the balancing elements, thereby allowing the individual to move up from a lower level of consciousness (herein TAPE-S) to a higher level of consciousness (herein TAPE-O) with minimum effort.

According to an embodiment of the invention, a balanced personality consciousness code that defines an idle state-of-mind is obtained when the ratio between the three elements is determined as follows: the dominant element reflects 50% of the individual's personally, the balancing element reflects 30% and the transformational element reflects 20%.

According to an embodiment of the invention, missing or negligible tones as appear on the octave scale with respect to the determined energy route reflects the required treatment in order to balance the personality consciousness code of the individual, so providing the missing or negligible tones to the individual helps to balance the personality consciousness code of said individual and to bring said individual to a higher LOC, and thereby enabling said individual to better handle stressful situations and diseases or to improve decision making processes.

According to an embodiment of the invention, the method further comprises generating content adapted for each specific personality code according to the dominant element of each code, and enabling to provide said content to the individual in order to balance the personality consciousness code of said individual.

According to an embodiment of the invention, the method further comprises identifying an element which drives or motivates the individual to perform an action, wherein said element is derived from the dominant element of said individual.

According to an embodiment of the invention, the method further comprises continuously measuring the LOC of the individual during a conversation between the individual and other person and allowing said other person to identify the current LOC of said individual, in order to provide said individual content that will enable to balance the personality consciousness code of said individual and as a result to improve in real time the ability to close a deal between said individual and said other person.

According to an embodiment of the invention, improving the ability to close a deal is done by continuously measuring the LOC of the other person and correlating the coherent of the tones on an octave scale between the personality consciousness codes of the individual and said other person.

According to an embodiment of the invention, the generated content is directed to show to the individual an imagined "future reality" with a product/service, using a simulation that is adapted to the dominant element in the personality code of said individual, thereby allowing said individual to "see in his mind", in a positive manner, the future use with the product/service.

According to an embodiment of the invention, the generated content is directed to emphasize the profit of the individual from a product/service, by introducing a social oriented comparative advantage based on a motive driven from the dominant element.

According to an embodiment of the invention, the personality consciousness code is determined by four roots elements T, A, P and E, that are presented on a consciousness scale, wherein one of said four elements, determines the dominate element, one determined the balancing element and one determines the transformational element, wherein the relations between the dominate element, the balancing element and the transformational element is such that a relatively slight change in the transformational element will result in the largest change in the dominant and the balancing elements, thereby allowing the individual to move up from the current LOC to a higher LOC with minimum effort, wherein the ratio between said elements is determined as follows: the dominate element reflects 50% of the individual personally code, the balancing element reflects 30% and the transformational element reflects 20%.

According to an embodiment of the invention, the method further comprises measuring the consciousness level of the individual includes using a set of questions, by performing the steps of:
  measuring the energy field of the individual by one or more sensing units while said individual answers to each question, wherein said measured energy field represent the objective feedback of said individual to each of the questions while the content of the answers represent the subjective response of said individual;
  detecting the dominant element of said individual from said measured energy field and accordingly detecting the personality code; and
  comparing the subjective response of said individual (TAPE-S) with the measured objective feedback of said individual (TAPE-O) with respect to the detected personality code for determining the consciousness level of said individual, wherein while the difference between said subjective response and said measured objective response is relatively high, then the consciousness level of said individual is determined as relatively low on the consciousness scale, and vice versa.

In another aspect, the present invention relates to a non-transitory computer-readable medium having instructions stored thereon that are executable by a computing device to perform operations comprising: a) storing, in a database, reference voice characteristics of different persons that represent acoustic information as expressed by human voice in a form of a time to frequency component relation, wherein said acoustic information indicative of dominant elements, three energy routes and extraversion-introversion personality traits; b) classifying the acoustic information into 12 different personality consciousness codes, based on the determination that each personality code includes a dominant element, a balancing element, a transformational element, an energy route and a personality trait, by using support vector machine that analyzes said acoustic information; c) receiving, by a computing system, data indicative of a sound energy generated by the voice of said individual; d) analyzing, by the computing system, said received sound energy in order to obtain voice characteristics from an electronic representation of said sound energy in the form of a time to frequency component relation; and e) comparing said obtained voice characteristics with the reference voice characteristics and determining the personality consciousness code of said individual by using the support vector machines, and using the obtained voice characteristics to determine the level of consciousness (LOC).

According to an embodiment of the invention, the operations of the non-transitory computer-readable medium further comprises generating feedback signals according to the transformational element in order to balance the personality consciousness code and to bring the individual to a higher LOC.

In another aspect the present invention relates to a system, comprising: one or more processors; and one or more memories having program instructions stored thereon that are executable by the one or more processing to cause the system to perform operations comprising: a) storing, in a database, reference voice characteristics of different persons that represent acoustic information as expressed by human voice in a form of a time to frequency component relation, wherein said acoustic information indicative of dominant elements, three energy routes and extraversion-introversion personality traits; b) classifying the acoustic information into 12 different personality consciousness codes, based on the determination that each personality code includes a dominant element, a balancing element, a transformational element, an energy route and a personality trait, by using support vector machine that analyzes said acoustic information; c) receiving, by a computing system, data indicative of a sound energy generated by the voice of said individual; d) performing, by the computing system, spectral analysis of said received sound energy in order to obtain voice characteristics from an electronic representation of said sound energy in the form of a time to frequency component relation; and e) comparing said obtained voice characteristics with the reference voice characteristics and determining the personality consciousness code of said individual by using the support vector machines, and using the obtained voice characteristics to determine the level of consciousness (LOC).

According to an embodiment of the invention, the system further comprises a feedback unit for providing content and/or transmitting acoustical signals to the individual according the transformational element resulted from the calculated values of each element of the personality consciousness code, thereby enabling to balance the personality consciousness code of said individual.

BRIEF DESCRIPTION OF THE DRAWINGS

In the drawings:

FIG. 1 is a table showing an example of scaling the levels of consciousness;

DETAILED DESCRIPTION OF PREFERRED EMBODIMENTS

Figure 2:
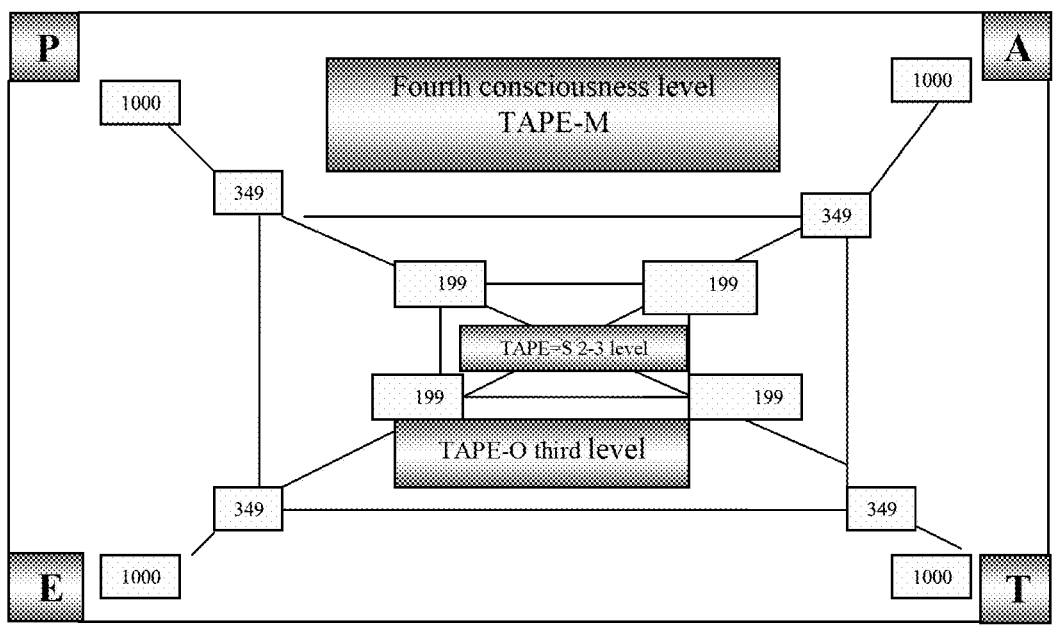
FIG. 2 schematically illustrates a level of consciousness graph in correlation with consciousness levels, according to an embodiment of the present invention.

The present invention relates to a universal system for measuring behavioral change in human consciousness that is based on a personal code. According to an embodiment of the invention, the system allows to measure human consciousness level through the components of one's voice. In one aspect, the system enables to measure and detect the personal consciousness code of an individual and accordingly to provide feedback to the user in order to improve the decision making processes or to determine the required method of treatment. The system can be used to identify the strengths and weaknesses of the user's personality by an objective feedback based on the user's (i.e., the subject) energy field, and not just by a subjective feedback as done in the prior-art. The system detects the subject's level of consciousness. No matter what type of typology is used, the system can identify the root elements of the personality, so that through a short test could a therapist, the user himself or even an organization that uses the system to receive information that will aid them to decide objectively or recommend them, of an efficient way of acting or operating for obtaining better decision making.

The method of the present invention is based on the common assumption that the human personality operates like a series of psychological functions, and that a human knows things that he does not always aware of, but they are expressed in the responses of his body (e.g., can be expressed by the user's voice).

While different combinations of such functions create different ways to receive and to produce information. Humans always strive for happiness and the joy of creation, to be balanced in the universe. It is well known that there are different personality types of people which drive or act by different types of energy, such as businessmen, inventors, leaders, employee, etc. Usually these energies are genetics. According to an embodiment of the invention, the energy that motivates or drive people is categorize into one of three main energy routes, which are defined as Dynamic energy people (d), Permanent (constant) energy people (pr) or Non-permanent (varied) energy people (n). Although each person is unique and form different combinations of these energy routes, most people have one dominant personality and energy route that characterizes them most accurately. According to an embodiment of the present invention, each energy routes d, p or n can be represented on an octave scale, as will be described in further details hereinafter and with respect to FIG. 8.

The terms "extroverted" or "extroverted personality" refers herein to a personality trait, where a person is usually motivates with respect to an external energy source, e.g., a person that easily interacts with other people, a friendly character. Extraverts people tend to enjoy human interactions and to be enthusiastic, talkative, assertive, and gregarious.

The terms "introverted" or "introverted personality" refers herein to a personality trait, where a person is usually motivates with respect to an internal energy source, e.g., a person who prefers privacy or one on one contact with other people and less prefer contact with a group of people.

The trait of extraversion-introversion is a central dimension of human personality theories.

Essentially a person aspires to play the game of life in maximum of security, awareness, control, pleasure and success. This is the goal of most people in their life; when one achieves this goal, the person "moves" with a great energy, think fast, achieves success in reality, creates reality, shares with others, full of joy, full of laughter, becomes lightness, achieves goals, etc., all of these great features become possible when the person comes to a relatively higher level of consciousness (e.g., move up from a LOC in the range of force to a LOC in the range of power, as shown in FIG. 1). However, many people live their life on an "automatic pilot" mode where they make their decision from their subjective self, which is usually located in the range of force in the LOC. Therefore one of the objects of the system and method of the present invention is to aid people to make decision from a relatively higher LOC.

FIG. 1 shows a table in which the levels of consciousness are represented by logarithmic figures based on the scale of Dr. Hawkins, i.e., it means 10 to the power of each figure (e.g., level 200 is not the absolute number 200. Thus, 200 on the scale, does not mean twice the magnitude of 100). Therefore, a small increment by a few points represents a huge increase in magnitude. For example, let's look at the values 175 and 200. Even though it's just difference of +25 in pts on the scale, according to the logarithmic terms this means that it will result in enormous improvements in one's well-being and state of life.

According to an embodiment of the invention, the suggested method is based on the assumption that there are four main elements which represent the individual personality code of a person (i.e., this code may refer to as the root or DNA-like personality code of an individual). The elements are defined as Trust (T), Achievement (A), Pleasure (P) and Empire (E) (i.e., refer herein as the TAPE elements of the personality code of an individual). These four elements are innate motivator personality codes for decision-making. These motivators emanate from the evolution of the brain. Also known as 'Dominant Attractors' which always pull in their direction. In other words, each element represent a different human survival mechanism that affect the decision making of a person. The terms "personality code" or "personality consciousness code" refers herein to a consciousness genetic code of an individual person that affects his or her decisions. The personality consciousness code of a person is the product of a combination of the four TAPE elements and the three energy routes (pr, d, n) that together provides 12 (i.e., 4×3) different possibilities of personality consciousness codes. The personality consciousness code of an individual can be detected by analyzing one's voice, as will be described in further details hereinafter.

Following is a more detailed description of the four TAPE elements of the personality code:
T—Represents the level of Trust of a person which can be positioned on the level of consciousness axis between Fear to Trust;
A—Represents the level of Achievement of a person which can be positioned on the level of consciousness axis between the inability of doing (i.e., depression) up to the desire for achievement;
P—Represents the level of Pleasure of a person which can be positioned on the level of consciousness axis between Sadness to Pleasure (joy);
E—Represents the level of Empire of a person which can be positioned on the level of consciousness axis between Egoism to Altruism (mastery or control).

By decoding the encrypted data of an individual's personality code, one can diagnose the strengths and weaknesses of that individual, the hidden potential inherent in that individual, and to obtain the optimal way to realize this hidden potential.

No matter what criteria or diagnostic typology of personal identification is used, the personality consciousness code can decode and show the strengths and weaknesses of an individual as well as the optimal way to treat that individual (i.e., to cause the user to move up in the level of consciousness scale). According to an embodiment of the invention, the level of consciousness scale is divided into three consciousness ranges (0-199, 200-349 and 350-1000) which are defined herein with respect to the following consciousness levels: TAPE-S (0-199), TAPE-O (200-349) and TAPE-M (350-1000), as schematically illustrated in FIG. 2.

TAPE-S—represents a subjective self-type (i.e., the "automatic pilot" type). Every human is the total resulting from his thoughts, feelings, life events and memories. TAPE-S represents people who act "automatically" by their subjective self and their decisions are taken from there. This represents the lowest ranges in the LOC scale (0-199). Many people usually located within this range on the LOC scale. This level can be defined as an instinct-based level (i.e., "attack and run").

TAPE-O—represents an objective type (i.e., the "self-pilot" type). A balance type of person, which acts by his own intelligence and imagination, has the ability to distinguish between true and false, between main things to subordinate, etc. TAPE-O represents people located in the middle ranges of the LOC scale (e.g., 200-349). This level can be defined as the logical thinking level (i.e., "think before attack").

TAPE-M—represent the complete personality type (i.e., the higher self). A person, that works with the past and with a vision to the future, and therefore can make correct decisions in a wise way. Someone who acts with maximum attention in the present and by that understands and remembers his life experiences and produces from them a pure study. This represents people located in the highest ranges in the LOC scale (350-1000)—the quantum thinking level (i.e., the fourth dimension).

TAPE-S, TAPE-O and TAPE-M each may represent the state-of-mind of an individual.

The following state-of-mind Table (1) summarizes the three consciousness ranges (i.e., TAPE-S, TAPE-O, TAPE-M) with respect to the level of consciousness:

TABLE 1

| | State-of-mind | | |
|---|---|---|---|
| | TAPE-S | TAPE-O | TAPE-M |
| Who rules | Automatic Pilot | Self Pilot | Higher Self |
| Mind level | Beta | Alpha | Theta and Delta |
| Behavior | Survival, act by fear, mostly egoism | Balanced, connected to reality | |
| Level of Consciousness | 0-199 $2^{nd}$-$3^{rd}$ level | 200-349 $3^{rd}$ level | 350-1000 $4^{th}$ level |
| World view | Frighten | Optimist | Harmony, joy |

It is assumed that each person has a TAPE-S level and a TAPE-O level. In some embodiments, the TAPE-S and TAPE-O levels of a person can be determined according to the person's voice by performing spectral analysis of the sound energy (e.g., when the person speaks), wherein the voice analysis can be used to detect the four TAPE elements, the three energy routes (p, d, and n), and the personality trait. For example, the energy route can be detected according to the coherent between the voice's tones on an octave scale.

According to an embodiment of the present invention, in order to allow a person to be in control (i.e., to move up and to act in the levels of TAPE-M), it is required to reduce the distance (i.e., the delta, the difference on the LOC scale) between TAPE-O and TAPE-S of that person to minimum, preferably to zero. By doing so, one can get himself closer to TAPE-M type. Preferably, the way to reduce this delta depends on the structure (or level) of the elements of each individual (i.e., the four T, A, P, E basic elements that characterized each individual person—the TAPE).

Figure 3:
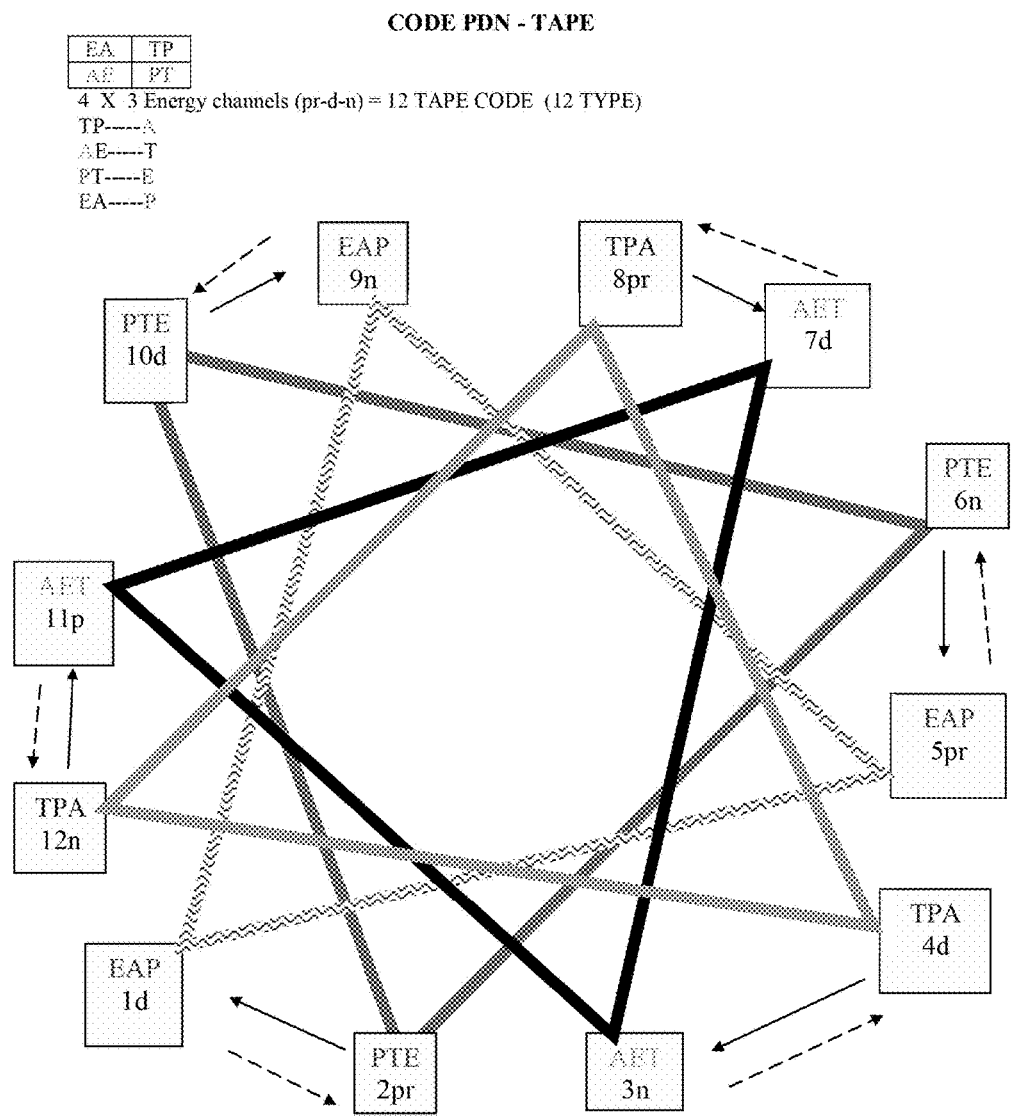
FIG. 3 schematically illustrates a personality consciousness code diagram in a circle form, according to an embodiment of the invention.

According to an embodiment of the invention, in order to increase the LOC of a person, the following element of the subject person should be identified:
The dominant element of a person—which is usually the prominent element in the human behavior (i.e., whether the person is motivated by the TAPE elements of the personality code). The dominant element can be detected by spectrally analyzing the person's voice for obtaining voice characteristics such as pace, intensity, speech tone, intonation, etc. (see table 3 for additional examples of voice characteristics);
The second element of a person—is the stabilizing element (i.e., the balancing). The second element depended on the dominant element. Based on the determination of the personality code, if the dominant element is "T" than the balancing is "P" and vice versa, if the dominant element is "A" than the balancing is "E" and vice versa, as shown with respect to FIG. 3; and The third element—is the hidden element of the person. This element is the transformational element. Based on the determination of the personality code, if the dominant element is "T" than the balancing is "A" and vice versa, and if the dominant element is "E" than the balancing is "P", and vice versa (as shown in FIG. 3). This is the element that can be used to treat a person (with minimum effort by the treated person) in order to allow that person to move up from the current LOC to a higher LOC. The relations between the elements (dominant, balancing and transformational) is such that a relatively slight change in the transformational element (i.e., the "critical point") will result in the largest change in the other two elements, and mainly in the dominant element.

According to an embodiment of the invention, the minimum effort refers to the type of treatment or to the relatively minimal change in the personality aspect that may influence a person and thereby cause that person to a relatively larger change in the dominant element.

According to an embodiment of the invention, an idle state-of-mind (i.e., according to the personality code the person is in a balanced state) is defined when the ratio between the TAPE elements are determined as 50/30/20 follows: the dominant element reflects 50% of the personally, the balancing element reflects 30% and the transformational element reflects 20% of the personality of an individual. For example, if a dominant element of a person is detected as Empire "E", the balancing element is then Achievement "A" and the transformational element is accordingly identified as Pleasure "P", then a relatively small change in the value of "P" will significantly increase the value of "E" as it constitutes 50% of the personality of the individual.

These elements are different from one person to another, and they draw the lines that affect a person's energy, stabilization or balance. As aforementioned defined, most people are on the three routes of energy: non-permanent (n), permanent (pr) and dynamic (d). Once the dominant element (from the four T, A, P and E elements) and the energy route (among the three defined energy routes) are detected, the system may generate a feedback to the person the (e.g., in form of acoustics signals), in order to increase the state-of-mind level from TAPE-S to TAPE-O with relatively minimum effort. For example, the system may generate acoustics/audible signals and play them to the person, wherein the audible signals may reflect the detected transformational element (e.g., may reflect missing frequencies as described with respect to numeral 81 in FIG. 8). Hearing the generated audible signals may fulfil the missing frequencies (according to the spectral voice analysis), and accordingly may cause that person to "move up" to a higher LOC. The system may continuously analyzes the person's voice and accordingly generate the audible signals until that person will reach a higher LOC or will reach a balanced state where the ratio between the TAPE elements is close as possible to 50/30/20).

According to some embodiments of the invention, in an addition to the spectral analysis of the person's voice, the dominant element and the energy route of a person can also be determined according to the person's answers to a set of questions, and optionally, other data related to the person (such as date of birth, time of birth, geographical location, etc). The set of questions can be built in such a way that each person can be distinguish and categorized according to the dominant TAPE element and the energy route. But, if the answers provided by the person are not correlated with the voice analysis, it means that person is not aware to his actual personality TAPE code and to the LOC.

An important feature of the present invention is the ability to find the transformational element and to use it to increase the LOC. This is a key element to rapidly change the state-of-mind from a low level to higher level. The trajectory of the transformational element is the energy of the optimal route to each particular person. This is the element to begin cleaning the roadblocks and fears that actually created the separation and the distance from the higher self of that person. The more a person is loaded with energy, the system may clean up more from the "extra armor" that hides the real personality of that person, and returns control to the person, from the "automatic pilot" (i.e., TAPE-S), to "my own self" (i.e., to TAPE-M).

In the prior art, most decisions of the people who make decisions, human resources filtering, and the like, use techniques which their feedback from a person was based on its TAPE-S only (i.e., on the subjective feedback from the person). However, such techniques do not reveal the hidden potential of the person or his real skills and abilities. In contrary, the system of the present invention indicates in what level the person is really positioned from a consciousness point of view—state-of-mind level (e.g., these reflects the abilities of the person that are hidden within him, and might revealed or expressed whenever the person will feel comfortable in a suitable job or environment).

According to some embodiments of the invention, TAPE-S can be determined by providing a set of questions on which the subject person needs to response/answer. According to the content of the response, the personality TAPE code is determined (although it may not reflect the actual personality TAPE code because the responses are based on the subjective act of the person). Therefore, in order to obtain the actual personality TAPE code of the person, the system of the present invention comprises one or more sensing units (e.g., a microphone or other voice capturing means), which measures the person's energy field (as well as optionally other physiological response). The sensing means can be any measuring unit capable of sensing, capturing, recording, or measuring human energy field such as human voice. In addition, other common types of human body sensing means can also be used to detect the personality TAPE code.

According to an embodiment of the invention, the system compares the measured response of the person's body (i.e., the objective response) with the subjective response of the person (i.e., it compares TAPE-O with TAPE-S) and accordingly it calculates the delta between them (i.e., it calculates "how far" is TAPE-O from TAPE-S of that individual person). In other words, this can used to understand how far is an individual from the actual state-of-mind level.

According to an embodiment of the invention, in order to identify the personal TAPE code of an individual, a TAPE code diagram or "map" can be used through which the three energy routes ("pr", "d", and "n") can be detected.

FIG. 3 schematically illustrates an example for such TAPE code diagram, according to an embodiment of the invention. The diagram shows possible directions of energy routes (wherein an extroverted personality characteristic is shown by the dotted arrows in the counterclockwise direction, and an introverted personality characteristic is shown by the non-dotted arrows in the clockwise direction) according to the three main types of human energy routes (wherein "pr" represents people having permanent energy, "d" represents people having dominant energy and "n" represents people having non-permanent energy). The personality code is represented by a circle form in which the personality code is formed three times in a circular manner, which gives a total of 12 options or combinations for defining 12 different basic personality codes. Each of the four elements (T, A, P and E) can connect with each of the energy routes pr, d and n (i.e., resulting in a total of 12 possible options of personality codes).

The following Table (2) summarizes the 12 personality codes as defined by the TAPE code and the energy routes with respect to the diagram of FIG. 3. Table (2) shows the three elements of each personality code, the energy route and the corresponding extroverted or introverted character of each code.

TABLE 2 the 12 Personality codes

| The code No. | TAPE elements | Personality trait | Energy routes p-d-n | Dominant element | Balancing element | Transformational element |
|---|---|---|---|---|---|---|
| 1 | EAP | Extrovert | d | E | A | P |
| 2 | PTE | Introverted | pr | P | T | E |
| 3 | AET | Extrovert | n | A | E | T |
| 4 | TPA | Introverted | d | T | P | A |
| 5 | EAP | Extrovert | pr | E | A | P |
| 6 | PTE | Introverted | n | P | T | E |
| 7 | AET | Extrovert | d | A | E | T |
| 8 | TPA | Introverted | pr | T | P | A |
| 9 | EAP | Extrovert | n | E | A | P |
| 10 | PTE | Introverted | d | P | T | E |
| 11 | AET | Extrovert | pr | A | E | T |
| 12 | TPA | Introverted | n | T | T | A |

According to an embodiment of the invention, there can be only a limited combination of connections between the dominant and the balancing elements, which, according to the personality code of Table 2 and as schematically shown in FIG. 3, can only be the elements couples (E and A, or A and E) or the couples (P and T, or T and P). E and A represent an extroverted personality, while P and T represent introverted personality.

Accordingly, finding the third element—the transformation element—depends on the extroverted energy or the introverted energy of the individual. In case the individual is an extroverted type, then the energy route moves in a counterclockwise direction (i.e., E and A, or A and E) along the personality code diagram of FIG. 3. On the contrary, in case the individual is an introverted type, then the energy route moves in a clockwise direction (i.e., P and T, or T and P) along the diagram.

According to an embodiment of the invention, the decoding of the personality code may involve the following procedures:
  Detecting the dominant element and the energy route (pr, d, n) of an individual person, by spectrally analyzing the person's voice;
  Once the dominant element and the energy route are detected, identifying the second element, the balancing, according to the couples E and A (or A and E), or P and T (or T and P) of the personality code; and
  Identifying the transformational element, wherein the identification of the transformational element is done according to the voice characteristics and outputs obtained from an octave filter, which enables to determine the trait of the person, i.e., whether the person has an extroverted personality (e.g., combination of a relatively high pitch and high speech mobility) or an introverted personality (e.g., combination of a relatively low pitch and low speech mobility). This provides the clockwise or counterclockwise movement as schematically illustrated in the diagram of FIG. 3. The transformational element is defined according to the identified energy route of the person and according to the direction detected based on the personality characteristics, i.e., for an extraverted type (A and E) will move counterclockwise and for an introverted type (P and T) will move in clockwise direction. Following this rule, we find that the transformational element of one type will be the dominant element of the next type on the circle-like diagram of FIG. 3, according to the movement direction described hereinabove.

Figure 4A:
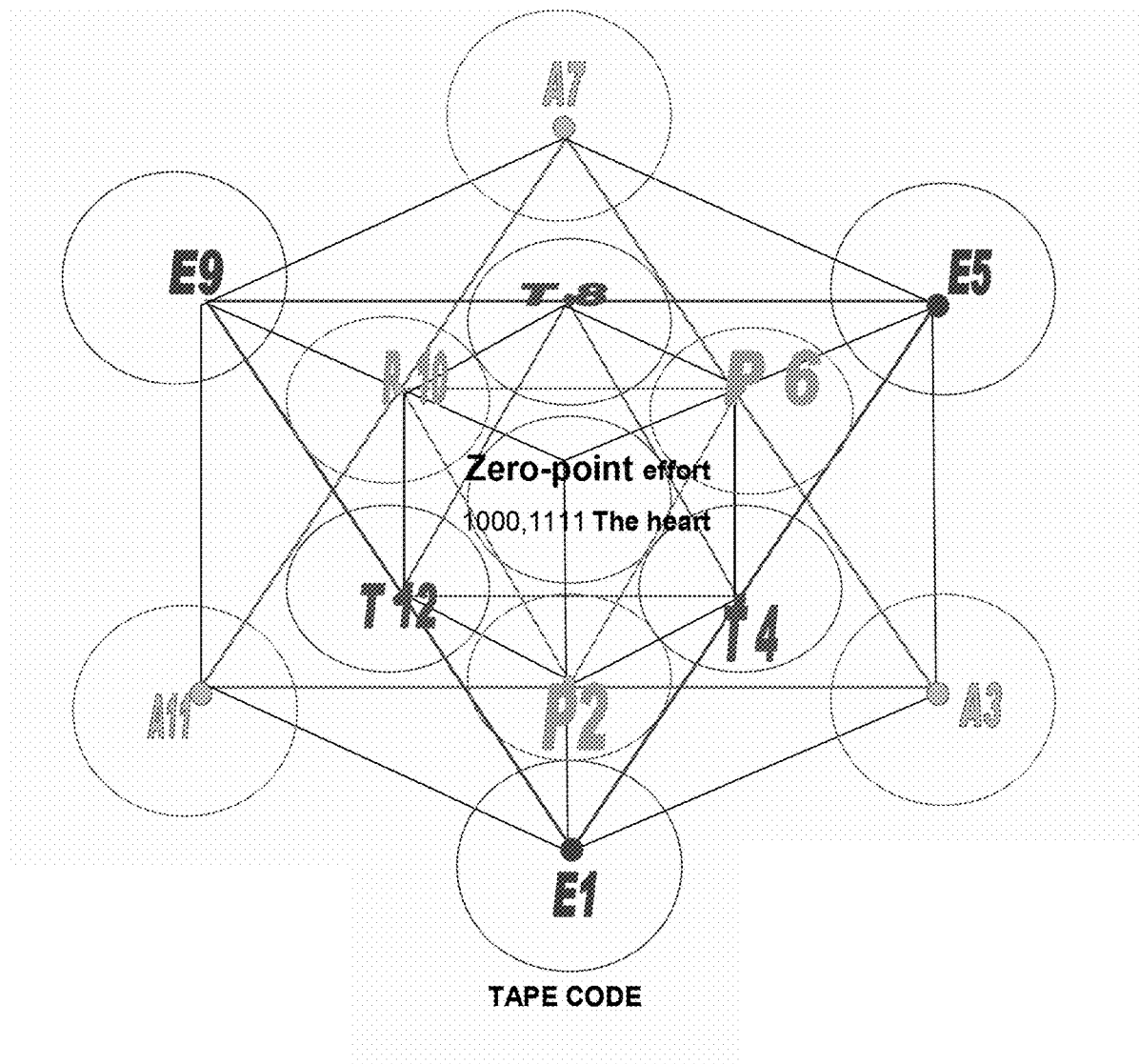
FIG. 4A schematically illustrates a personality consciousness code diagram presented in a Metatron's cube model, according to an embodiment of the invention.
Figure 4B:
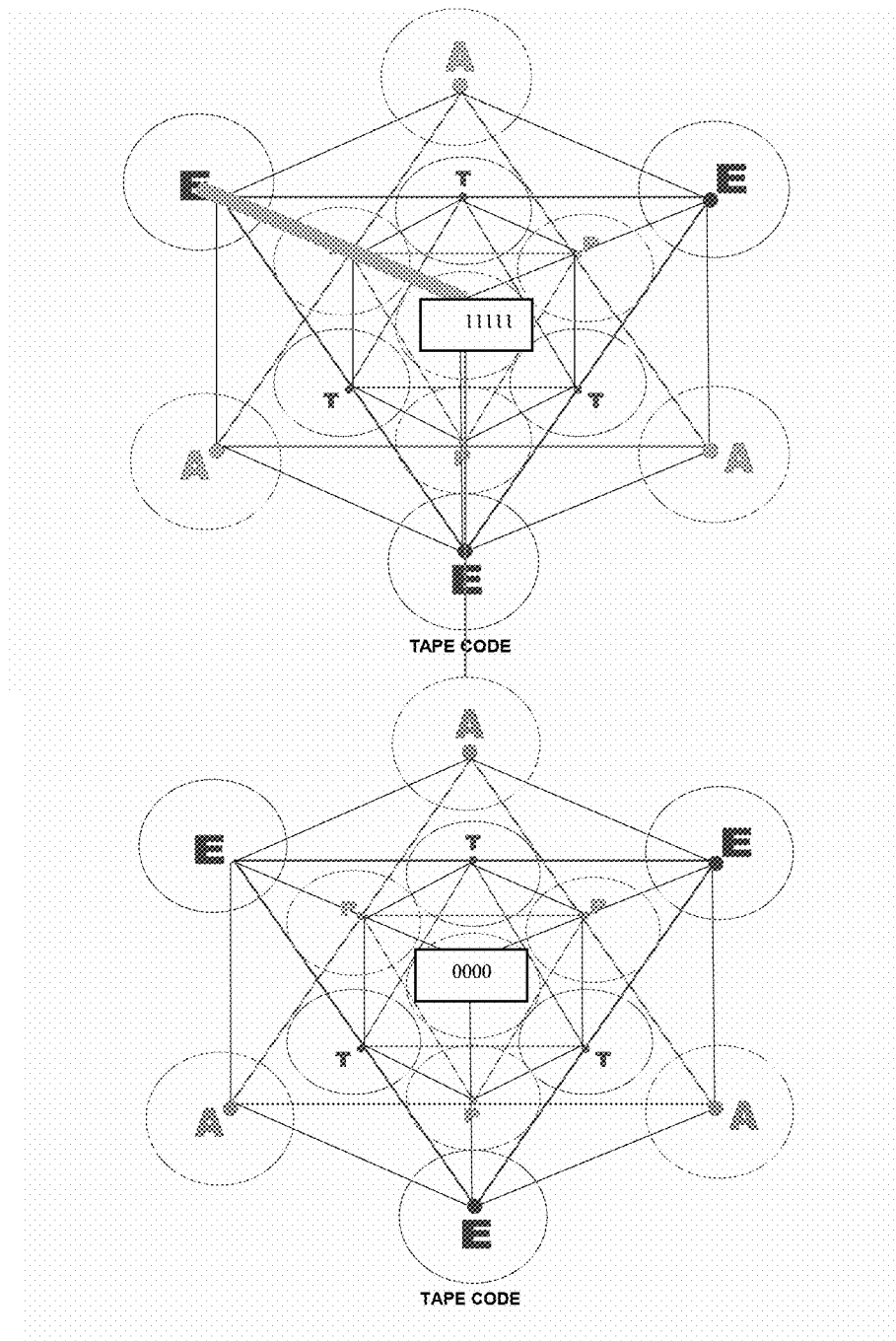
FIG. 4B schematically illustrates the transformation from one dimension to another using the Metatron's cube model.

According to an embodiment of the invention, the personality code diagram can be presented in form of a Merkava model (i.e., a form of 3D star of David) or in form of a Metatron's cube model as shown with respect to FIGS. 4A and 4B. The Metatron's cube represent a three dimensional module of two Stars of David, which represents a box within a box or a cube nested within a cube. Each circle represents a node, wherein a three pairs of the elements A and E represent nodes on the external cube and a three pairs of the elements P and T represent nodes on the internal cube. Two other nodes 0000 and 1111 represent the "heart" of the Metatron's cube (these two nodes can be seen on FIG. 4B as they appear in different dimensions, and they demonstrate the transfer or the bridge between one dimensions to the other). A maximum balanced personality code of a person is obtained when the personality code is located on these "heart" nodes (i.e., a person having a relatively high LOC). Therefore, one of the objects of the present invention, is to identify (e.g., this can be calculated by dedicated mathematical model installed within the software used by the system of the present invention) where a specific person is positioned on the Metatron's cube as well as the energy direction (i.e., the location of the detected personality code of that specific person and the direction required to move toward one of the "heart" nodes), and what type of treatment that person needs in order to bring him towards the "heart" nodes (i.e., to increase the LOC of that person).

According to an embodiment of the invention, after a subject person has been diagnosed by the system of the present invention (i.e., the three individual personality code of the subject were detected—the dominant, the balancing and the transformer), the subject's personality code can be positioned on the nodes of the Metatron's cube and accordingly the shortest route and its direction to one of the "heart" node can be calculated (e.g., by using Boolean algebra functions, wherein each node is represented by 4 digits combination of the two values "0" and "1", Gunn square, Fibonacci numbers, etc.). The shortest route reflects the minimum effort a person needs to do (i.e., treat or "fix") in order to move up to a higher LOC. The minimum effort is represented by the detected transformation element of that person (i.e., this is the element that should be treated or "fixed" in order to move up to a higher LOC. The treatment can be any suitable way of treatment, such as psychological, alternative medicine, coaching, vibrational medicine or vibrational therapy, acoustic signals, etc.).

Figure 5:
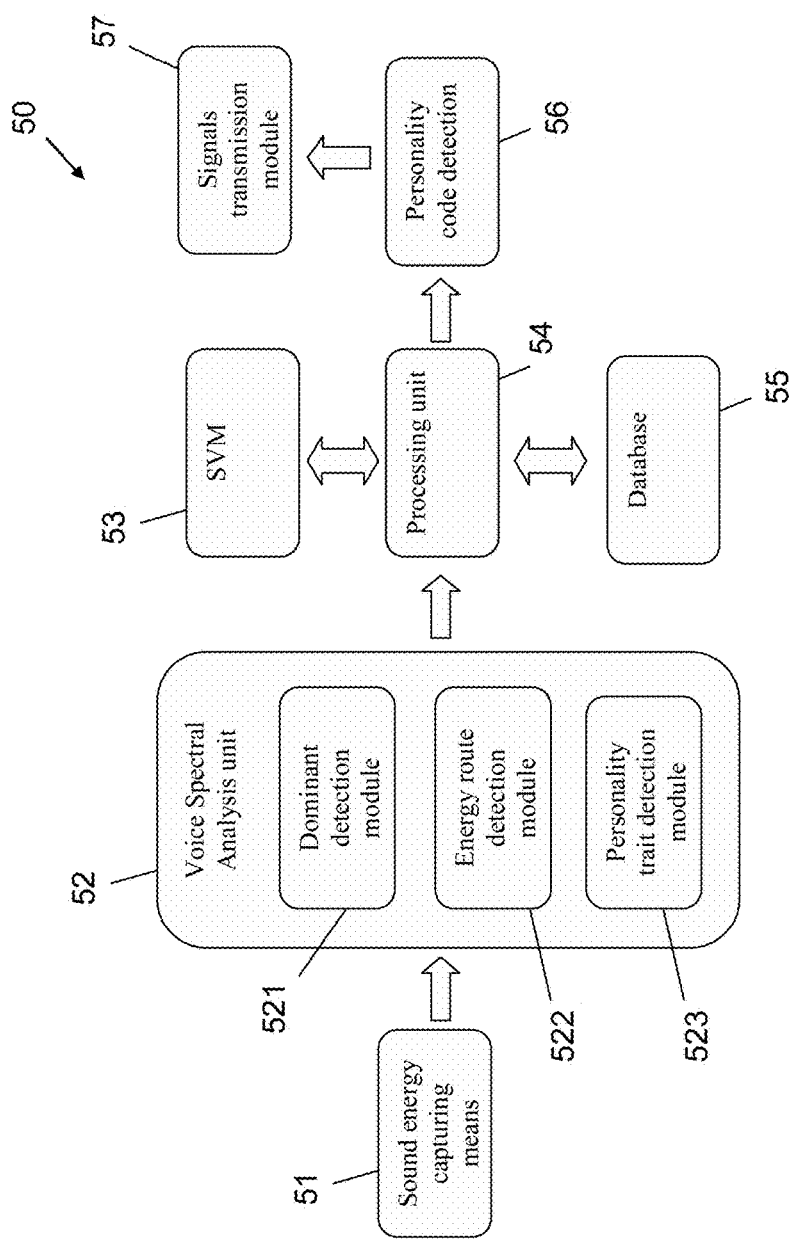
FIG. 5 schematically illustrates a system for detecting a personality consciousness code of an individual, according to an embodiment of the invention.

FIG. 5 schematically illustrates a system 50 for detecting a personality consciousness code of an individual, according to an embodiment of the invention. System 50 comprises sound energy capturing means 51, voice spectral analysis unit 52, a machine learning module 53 such as a support vector machine (SVM), a processing unit 54, a database 55, personality code detection module 56 and a signals transmission module 57 for transmitting acoustical signals to a person based on the transformational element of the personality code.

Voice spectral analysis unit 52 includes a dominant detection module 521 for detection of the dominant element from different voice characteristics of a human voice, an energy route detection module 522 that may use an octave filter to detect the energy route through an octave scale, and a personality trait detection module 523 for detection of the extroverted/introverted personality component of the personality code by using speech characteristics such as levels pitch and speech mobility.

According to an embodiment of the invention, the system captures sound energy (e.g., human voice) that is transmitted through air (or other medium) as a traveling pressure wave. The system analyzes the captured sound energy (i.e., a person's voice) by using spectral voice analysis in order to find the TAPE elements and the energy routes. The analysis includes dividing the captured sound energy into time units (e.g., about 0.3 milliseconds) and summing the appearance of a tone in each octave (i.e., counting how many times a specific tone from the 12 notes of an octave appears). For example, a western octave scale can be used (i.e., frequencies from 16.35 Hz to 8372.02 HZ). The octave may represent the interval between one acoustical pitch and another, where the pitch refers to a perceptual property of sounds that allows their ordering on a frequency-related scale.

Figure 8:
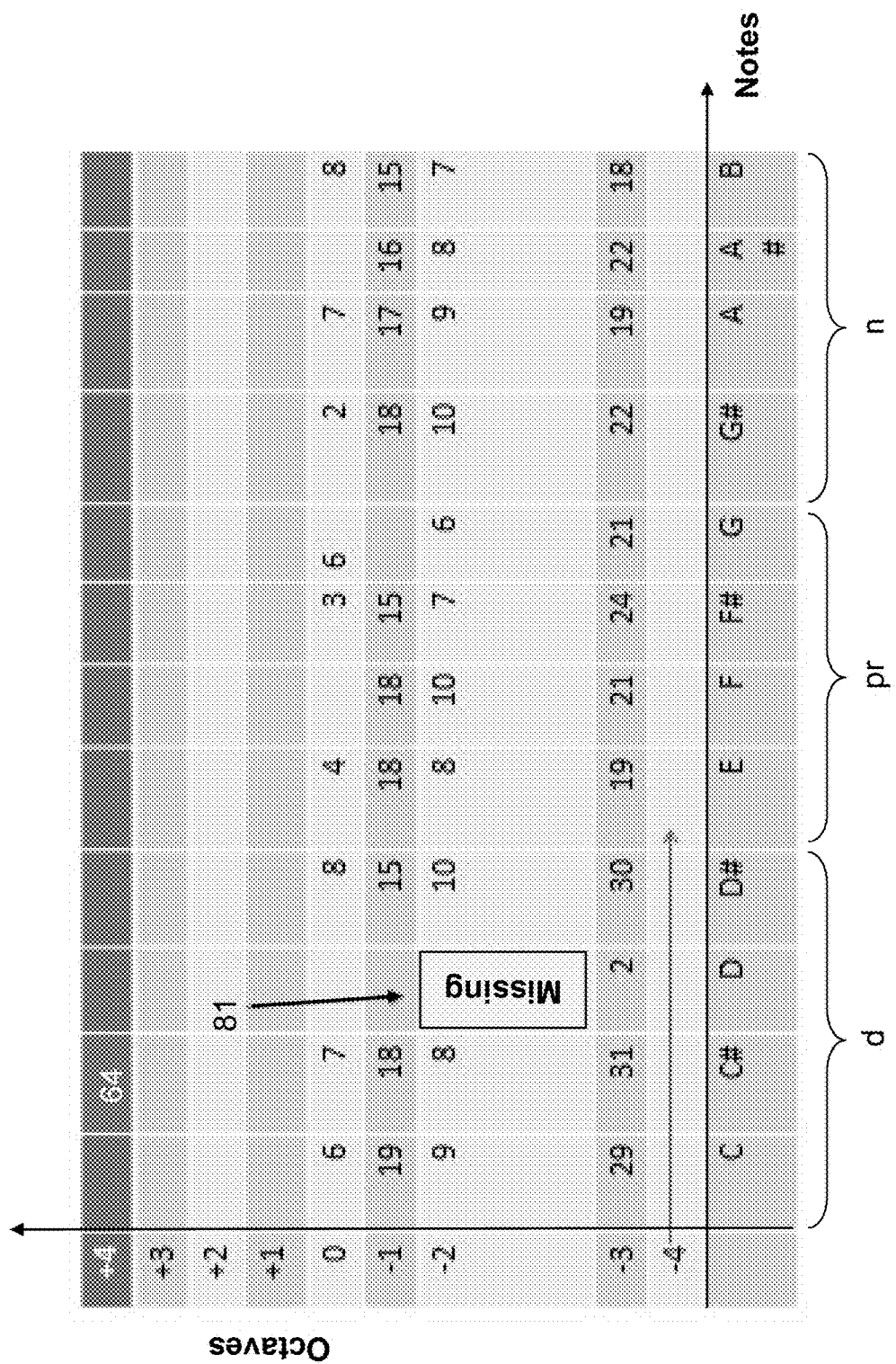
FIG. 8 schematically illustrates an example for an octave scale on which the three main energy routes (p, d and n) are represented.

FIG. 8 schematically illustrates an example for the representation of a sound energy on an octave scale, according to an embodiment of the present invention. In this embodiment, the three energy routes "d" (dynamic energy), "p" (permanent energy) and "n" (non-permanent energy) are each represented by a group of 4 notes as follows: "d" is represented by notes C to D#, "p" is represented by notes E to G, and "n" is represented by notes G# to B. The octaves are presented from −4 to +4. According to the example of the voice spectral analysis shown in FIG. 8, it can be seen that the highest values appear in the range of the notes C to D#, and therefore the energy route of that person (the one that his voice has been analyzed according to this example) can be defined as "d" (i.e., as a dynamic energy person). In addition, it can be seen that the note D in octave −3 is very low with respect to the other tones in "d" group and in octave −2 is completely missing.

According to an embodiment of the invention, when the notes of a group in an octave (in the main energy route of an individual—in this example the person main energy route is defined as "d") are similar (i.e., a Fast Fourier Transform can show that they are coherent), the person is in a balanced state (e.g., in octave −3 it can be seen that the values of the notes in the group that represents the "d" are very similar, which are 29, 31 and 30, except tone D which is negligible, and therefore the tones are coherent). As much as there are missing tones, the notes are less coherent, which indicates that the person is less balanced. It is assumed that each personality code has tones and octaves that define it, as shown with respect to the example of FIG. 8. For example, the values in FIG. 8 may refer to E=48%, A=32%, P=15% and T=5%, this also indicates that there is a balance between the elements (i.e., coherent) as it reflects the optimal ration of 50%, 30% and 20% between the elements of the personality code.

The voice spectral analysis may further include emotion detection. For example, as will be appreciated by a person skilled in the art, Support Vector Machines (SVMs) can be used to classify opposing emotions. The emotion may indicate a change in the LOC of an individual, e.g., from fear to secure, after providing that individual the transformational element by using acoustical signals or by using words or sentences that are relevant to the personality code as described in Table 4. For example, the system may generate an acoustic signal that may fulfill a missing tone (as indicated by numeral 81 in FIG. 8).

The system includes a database that comprises definitions of certain voice characteristics, octaves and tones that are related to the 12 personality codes. The system may further use machine learning techniques such as support vector machine (SVM) to analyze the data in the database and classify voice characteristics into personality codes, or to use artificial neural network (ANN) as a part of a machine learning in order to estimate or approximate functions that can depend on a large number of inputs of previously detected personality codes (i.e., a system that learn from data).

Figure 6:
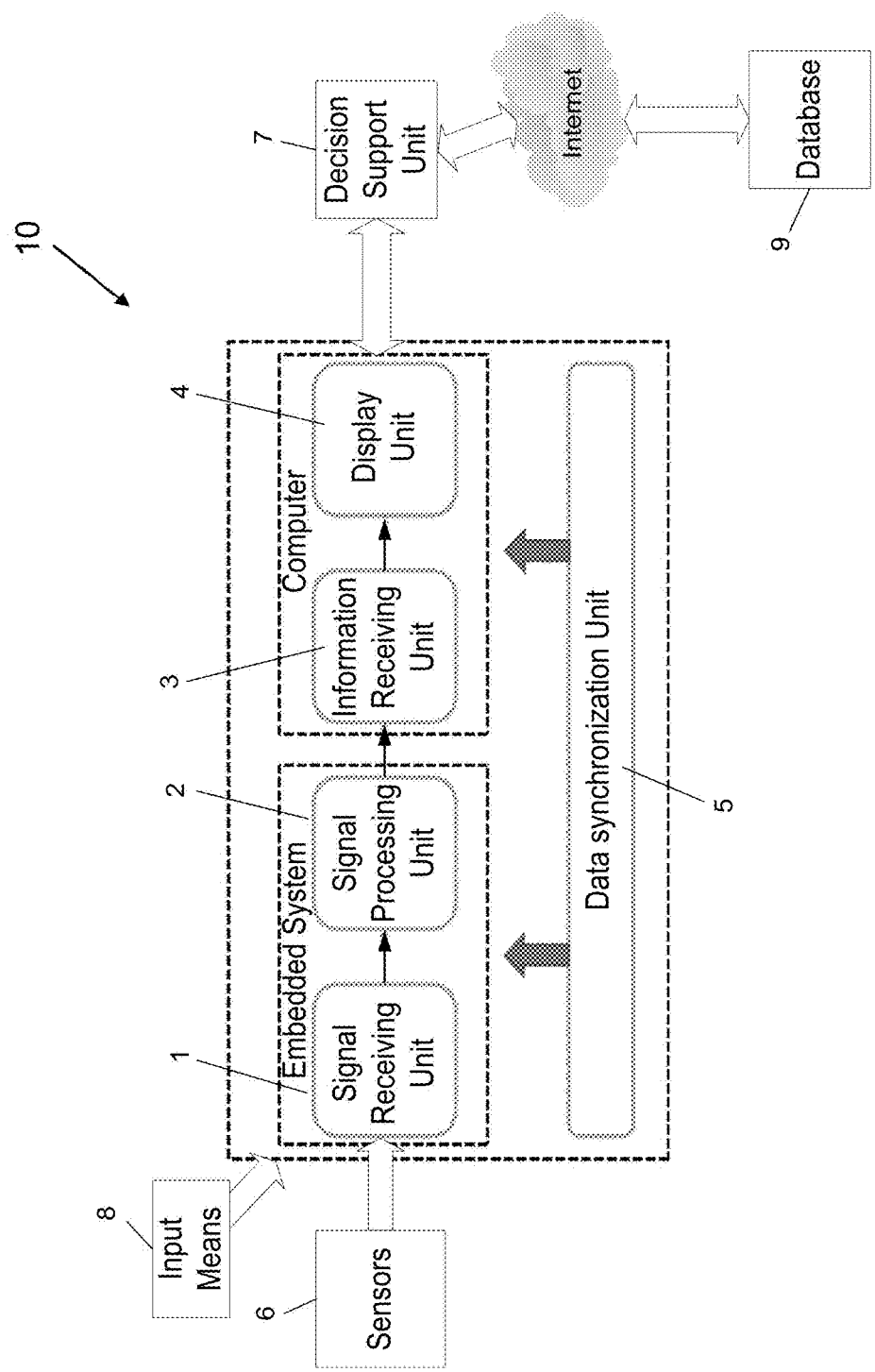
FIG. 6 schematically illustrates a block diagram of a system for consciousness level measurement, according to an embodiment of the invention.

Referring now to FIG. 6, a system 10 for detecting personality code and LOC is shown in a block diagram form, according to an embodiment of the invention. System 10 comprises a Signal Receiving Unit (SRU) 1, Signal Processing Unit (SPU) 2, Information Processing Unit (IPU) 3, Display Unit (DU) 4, Data Synchronization Unit (DSU) 5, sensing means 6, input means 8 and an optional Decision Support Unit 7. The sensing means 6 are used for capturing sound energy, such as human voice, which are processed by the Information Processing Unit 3 in order to detect the voice characteristics, the octave and the tones.

System 10 operates as follow: One or more one sensing units 6 are set to sense or measure the subject's body vibrations or energy field. Optionally, a sensing unit can be used to measure other physiological body response of the subject, such as Biosensor to measure the Biofeedback Data, which is the Electro-Dermal Activity and Electrical Conductivity of the skin of the subject and it's Temperature (e.g., the subject's hand).

Display Unit 4 introduces pre-defined set of questions (e.g., questionnaire for categorizing the subject personality) to the subject, treatment suggestions and decisions. Input means 8 are one or more data input devices which are used to receive the subject's response to the introduced questions (i.e., the subjective response—subject's TAPE-S). During the subject's answers to the questions, signal receiving unit (SRU) 1 receives input signals from sensing unit 6 as electromagnetic wave variations (this received signals will be processed and translated into the TAPE-O representation of the subject—the objective response). SRU 1 amplifies the received analog input signal, digitizes that signal and converts it into a digital signal. Signal Processing Unit (SPU) 2 receives the converted digital signal, processes the received digital signal and outputs data, which represent the subject's physiological body response (e.g., energy field or other body vibrations), to the Information Processing Unit (IPU) 3.

IPU 3 receives the data from SPU 2, analyzes the received information and makes mathematical computations and analysis. The IPU 3 also sends data to Display Unit 4 for showing the subject or operator of system 10 the mathematical analysis results and optionally the decision support recommendations from Decision Support Unit 7. Data Synchronization Unit 5 synchronizes the received signals from sensing unit 6 and the data received from the input means 8 (i.e., in order to compare between the subject subjective response to the set of questions and the subject's body vibrations).

Sensing unit 6 can be any type or combination of sensors or devices suitable to measure or record the human energy field as vibrations, such as electromagnetic field sensors, SQUID magnetometer which is capable of detecting tiny biomagnetic fields associated with physiological activities in the body, Kirlian and enhanced computer photography, etc. Input means 8 can be any suitable pointing device, such as a Personal Computer (PC) mouse. IPU 3 can be any suitable computational device, such as a PC, a laptop, a mobile computing device and the like, or it can be a dedicated computational device provided with dedicated software for performing the required analysis and processing, as aforementioned hereinabove.

IPU 3 is connected to or comprises memory means (not shown) for storing relevant information and the software programs required for calculating, identifying and categorizing each subject according to the method of the present invention, such as:

- a program for determining a consciousness scale, wherein in each value on that consciousness scale is a logarithmic value representing a frequency; a program for determining the four personality elements Trust (T), Achievement (A), Pleasure (P) and Empire (E);
- a program for setting the ranges of each of the four elements on the consciousness scale; the dominant element, the balancing element and the transformational element; a program for determining the pairs of a dominant element and a balancing element (i.e., E, A and P, T);
- a program for determining three energy routes for categorizing each subject into one of three energy routes by defining 12 personality types according to combinations of the four elements with the three energy routes;
- a program for providing a set of question to each subject for categorizing each subject into one of the 12 personality types, and other required information and processing as aforementioned hereinabove; and
- a program for calculating the difference between the subjective response and the objective response of a subject, by comparing the subjective response of the subject in correlations with the objective response of that subject, thereby determining the consciousness level of the subject, wherein while the difference between the subject response and the correlated objective response is relatively high then the consciousness level of the subject is defined as relatively low, and vice versa.

System 10 can be implemented within any suitable PC system, notebook, cellular phone, hand held device, and the like.

According to one embodiment of the invention, the system of the present invention is implemented over a network which incorporates server and clients. In such implementation, the software programs (or at least part of them) and one or more set of questions are stored and operated from a remote server (e.g., by processes running on the server side). For example, the server can be a web server using standard protocols such as TCP/IP, UDP, HTTP, etc. and the clients can be applications running on computers or other terminal units (e.g., PC, laptop, notebook, tablet PC, various kinds of mobile devices such as smart phones, iPhone, etc). The applications can be either dedicated User Interface application or a dedicated website suitable to interface with the web server.

In such embodiment, the data input device(s) (i.e., input means 8) and the one or more sensing units 6 are connected or part of the computer or other terminal units. Accordingly, the data input device(s) is used for collecting data which represents the subjective response provided by the subject to an introduced set of questions (i.e., which are used for determining the personality type of the subject), and the sensing units 6 are used for measuring the energy field of the subject while the subject answers to each question (wherein the measured energy field represents the objective response of the subject to the set of questions). The collected data and the data representing the measured energy field can be sent to the web server in order to perform the required calculation and analysis. Alternatively, at least part of the calculation and analysis can be performed locally by utilizing the terminal unit resources (depend on the terminal unit resources).

According to an embodiment of the invention, the system further comprises one or more treatment database(s) for storing data related to different ways of treatment to provide to the subjects. The treatment database can be either located locally in relation to the system 10 or remotely to system 10. In case the treatment database is located remotely to system 10, then the treatment database can be accessed via the Internet or via other network protocols. System 10 may include a database 9 which is remotely connected to system 10. In this figure, the database 9 communicates, via the Internet, with decision support unit 7.

According to one embodiment of the invention, the treatment provided to the subject via the treatment database is provided in real-time while the subjected is being tested by system 10, thereby allowing system 10 to provide an adaptive treatment to the tested subject according to the progress of the subject during the test.

The system of the present invention can be used as a decision making support system, which universally diagnoses of human behaviors and gives a diagnosis and recommendations to the subject. The diagnosis and recommendations are based on analyzing the difference between the subjective response and the correlated objective response of the subject and on the identified personality elements of the subject. According to an embodiment of the invention, whenever the difference between the subjective response and their correlated objective response is relatively high then generally the consciousness level of the subject is relatively low, and whenever the difference between the subjective response and their correlated objective response is relatively low then generally the consciousness level of the subject is relatively high.

Such recommendations provide the subject with a preferred way of act according to the system's diagnosis (e.g., in business decisions). Alternatively, the recommendation provides the subject with treatment suggestions which may shorten the way to raise the level of consciousness of that subject.

The system of the present invention used to detect the level of human consciousness, using calibrated values with a logarithmic sequence, as aforementioned hereinabove. The device of the present invention is also a code decoder of the individual transformation required for each person who using the system to increase his own LOC.

The system detects or identifies the basic components that determine the level of consciousness: the dominant, the balancing and the transformational. Where, transformational, is the key for maximizing human capabilities in all aspects of life. The personality code suggested by the present invention is a decoder, or a universal code of personality diagnosis, as all the criteria which are used by known methods which are used to diagnose personality, or discover human types, can be "dressed" on the TAPE code. As this TAPE code simply finds the strongest element in personality of a subject type. The TAPE code allows identifying the motive inherent in every person and starting to move in the shortest route, from a state of power, into state of strength (i.e., a higher LOC).

Optionally, the technique to identify aspects of each subject can be accompanied by a written test in addition to the spectral analysis that identifies the strengths and weaknesses of the subject as well as the subject's personality code. The identification is done by diagnostic and detection of the subject's objective response based on the spectral analysis, in correlation with the subject's subjectivity answers to the written test.

According to an embodiment of the invention, system 10 may be provided with two type of sensing units, a human energy field detection unit (e.g., Kirlian photography equipment) and a physiological body response sensing unit (e.g., Applied Kinesiology testing equipment, such as the "Touchstone" by Vitascans Inc. or other electronic muscles or energy tester, such as GSR, EMG, EEG, etc). Such a muscle tester taps into the subject body's subconscious to detect how the subject really feels about a particular emotional issue or personal interaction (e.g., are you happy? And the answer usually should be "Yes" or "No"). Accordingly, the set of question (i.e., the written test) is based on yes/no answers (i.e., "1" or "0"). In this embodiment, the system (e.g., the electronic muscles tester) should be calibrated for each individual subject, in order to determine a threshold level for "Yes" or "No" response of the subject's body (e.g., the strength of finger pressure readings or muscle response might be different from one subject to another). The system can be calibrated by introducing the subject at the beginning of the test verifying questions, such as "is your name John?", "do you live in New-York?", and the like. Optionally, the calibration can be performed by other sensing means, such as the Kirlian photography equipment that provides data which represent the energy field of the subject.

Closing

Figure 7:
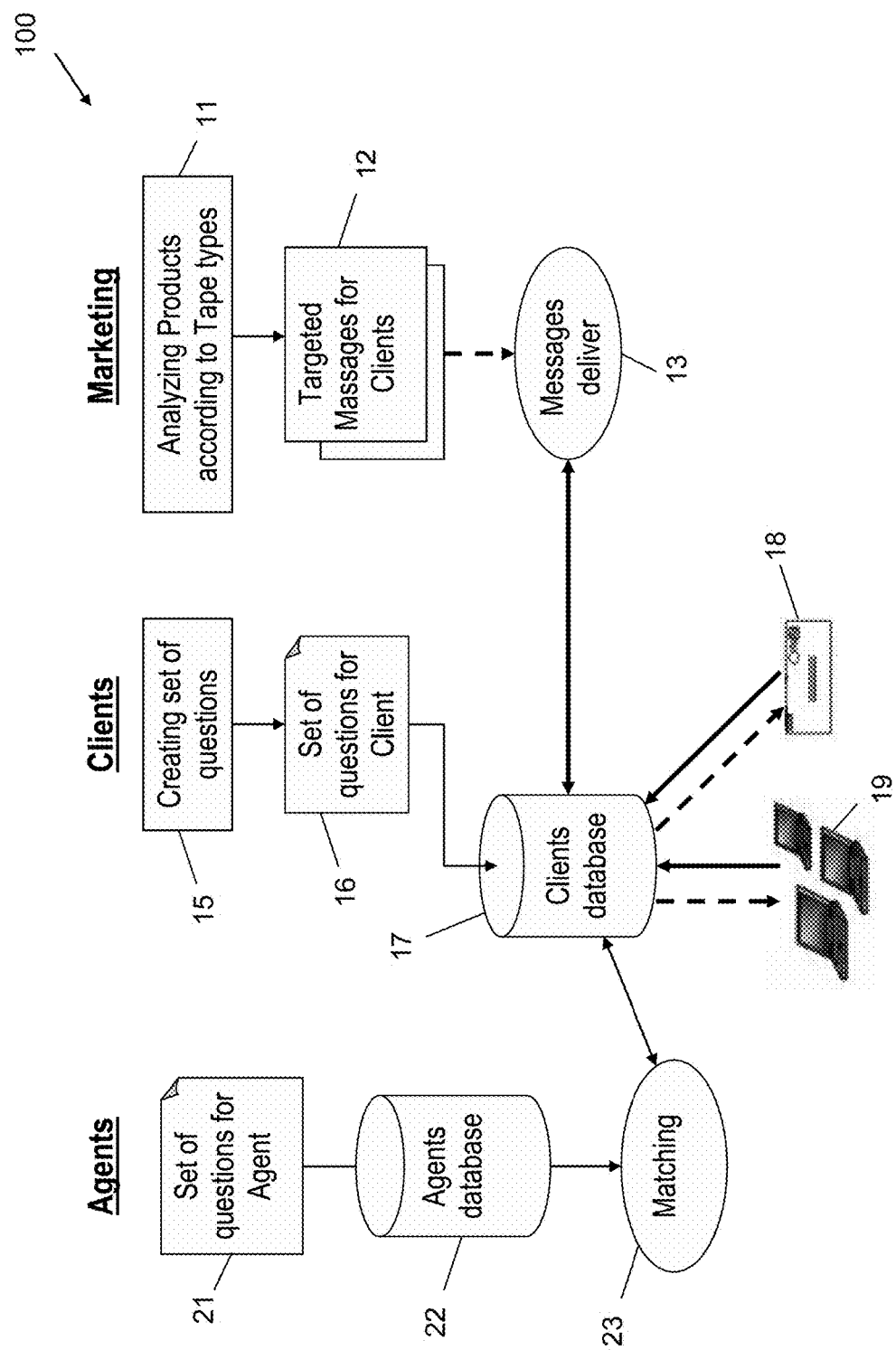
FIG. 7 schematically illustrates a matching system between clients and agents, according to an embodiment of the invention.

According to an embodiment of the invention, the system can be used for matching between persons, e.g., for business and marketing propose, for matching between clients and targeted marketing messages or between clients and company agents, such as salesman, for matching between student and teacher, for matching between a man and a woman, etc. FIG. 7 schematically illustrates an example for such a system 100 for matching between clients and agents and products based on the TAPE code personality type diagnosis of the present invention.

System 100 may comprises the following matching channels, the clients' channel, the marketing channel, and/or the agents' channel. The clients channel comprises the following steps:

Building (block 15) one or more sets of questions for identifying the dominant element of each client. Optionally, each set of questions is directed to different type of clients population (e.g., demographic location, age, and the like);

Providing (block 16) set of a questions to each client, via any applicable communication method, such as while a client visit in a shop, a webpage, etc., and according to clients answers to the set of question, categorizing each client profile according to at least the dominant element; and Storing each categorized client in a clients' database 17.

The marketing channel comprises the following steps:

Analyzing (block 11) the way of introducing the same product according to each TAPE personality type as defined by the method of the present invention;

Generating (block 12) targeted messages for each personality type; and

Matching between generated targeted messages and the clients according to their stored categorized profile and delivering (block 13) the generated targeted messages to these clients. For example, via SMS, e-mail 18, advertisement on a webpage 19, etc.

The agents channel comprising the following steps:

Providing a set of questions (block 21) to each agents for categorizing each agent according to the 12 personality TAPE types;

Storing each categorized agent in an agents' database 22; and

Matching between agents (stored in database 22) and clients (stored in database 17) having the same dominant personality type, thereby increasing the chances for "closing" a transaction. Of course, this is based on the assumptions that persons having matching personality type code can better interact.

Figure 9:
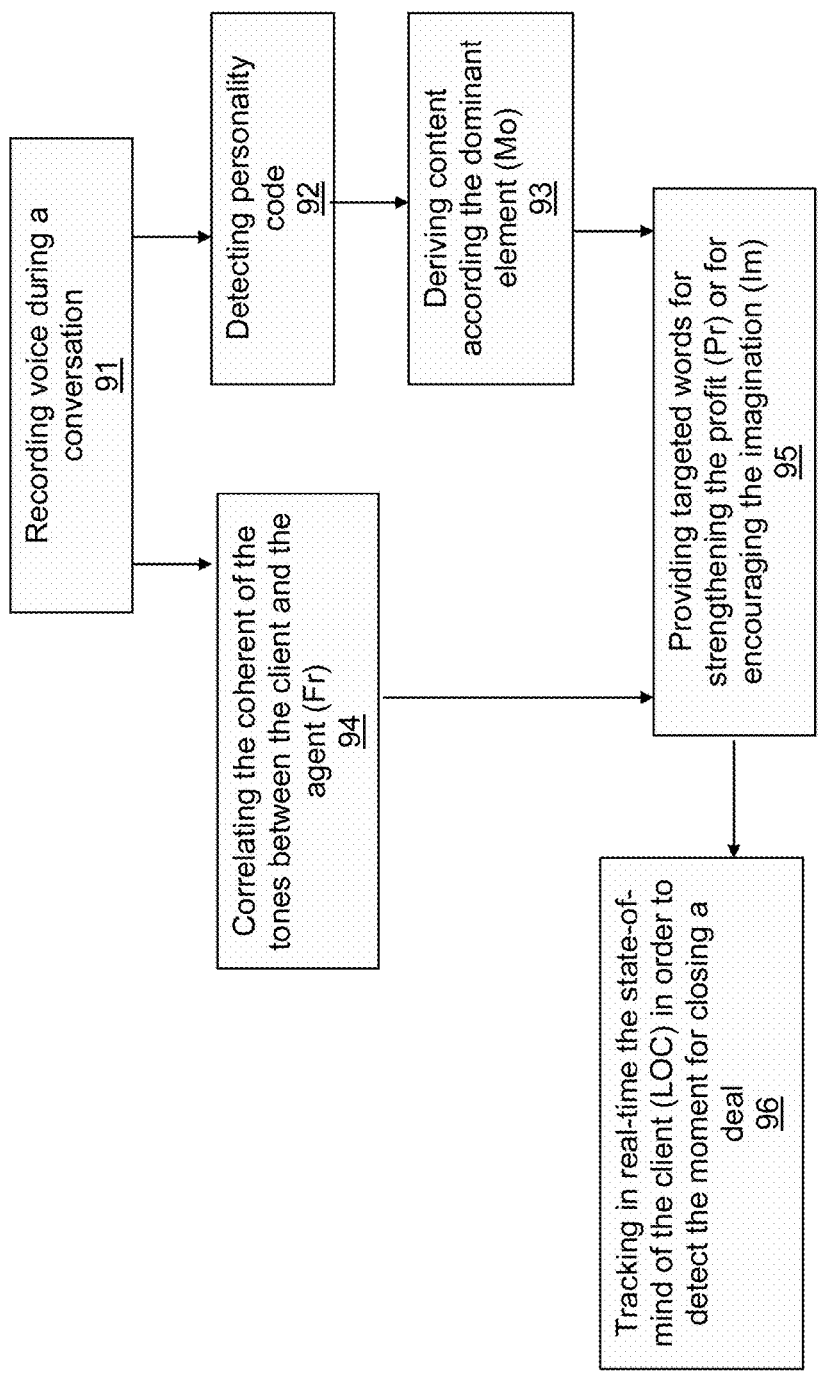
FIG. 9 schematically illustrates a flowchart showing a deal closing procedure between a client and an agent, according to an embodiment of the invention.

FIG. 9 schematically illustrates a flowchart showing a deal closing procedure between a client and an agent, according to an embodiment of the invention. The system continuously records and detects the personality code and LOC of a client (blocks 91, 92).

If an agent can recognize the dominant element of a client, then the agent can scientifically increase the chances of "closing" (i.e., succeeding in executing a transaction with that client, e.g., to sell that client a product or service). This can be done by identifying at least one of the following four elements Mo, Fr, Im, Pr:

(Mo)—Identifying what parameter(s) might drive (or motivate) the client to perform an action (e.g., drive or encourage the client to buy a specific product) as derived from the dominant element of the client as detected by the personality code (block 93);

(Fr)—correlating the coherent of the tones (on the octave scale) between the client and the agent (block 94);

(Im)—Showing to the client an imagined "future reality" with the product/service, using a simulation that is aimed to the dominant element of the client and the parameter(s) that might drive him, in order to allow the client to "see in his mind", in a positive manner, his future use with the product (block 95), as also shown in the examples of table 4; and (Pr)—Emphasizing the client's profit, by introducing the society's comparative advantage based on his motive (from the dominant element), thereby raising the client's level of satisfaction to be greater than the cost he need to pay for the product (block 95), as also shown in the examples of table 4.

As all these four elements (Mo, Fr, Im, and Pr) are directly related to each other, and a function of them (all together or at least part of them) enhance or increase the chances in succeeding with the "closing" (e.g., f(Mo, Fr, Im, Pr)="closing"). "Closing" can be obtained when the system detects that the client personality code becomes essentially balanced (i.e., ratio of 50/30/20) during the conversation with the agent. The system continuously analyzes the client's voice during the entire conversation.

The system tracks the LOC and personality code balancing during the conversation (block 96), so when the personality code is detected as balanced indicating the agent that it is time to close the deal.

For example, the parameter(s) that might drive or motivate the client to by a specific product can be as follows (assuming that such parameters which are aimed to the dominant element may better drive or motivate the client to purchase the specific product):

if the dominant element of the client is Trust (i.e., "T") then the agent should emphasis to the client one or more parameters which are related to the trust aspects of s specific product, such as safety of the specific product, manufacturer guarantee, the product is manufactured by a leading company in the field, etc.;

If the dominant element is Achievement (i.e., "A") then the agent should emphasis to the client one or more parameters which are related to the achievement aspects, such as what is the profit for the client from the product, the benefit from the product, special low price, etc.;

If the dominant element is Pleasure (i.e., "P") then the agent should emphasis to the client one or more parameters which are related to the pleasure aspects, such as the beauty of the product, pleasant shopping experience, etc.; and If the dominant element is Empire (i.e., "E") then the agent should emphasis to the client one or more parameters which are related to the client ego, such as whether the product is exclusive, what the product will do for the client, etc.

As aforementioned hereinabove, the technique to identify aspects of each subject is accompanied by a written test and a physiologically test that identify the strengths and weaknesses of the subject as well as the subject's personality type. The identification is done by diagnostic and detection of the subject's objective response based on the sense or response of the subject's body to the physiologic test, in correlation with the subject's subjectivity response to the written test. Based on the TAPE model the system detects the subject's level of consciousness. The system is a universal diagnosis for the human types and their level of consciousness. In some cases for matching purpose, the written test (i.e., the set of questions) can be used to detect the dominant element of the TAPE personality types of a subject without any physiological test. For example, this may occur when one of the matching sides is a client remotely located from the system, thus the client can answer only to a written test (e.g., via an Internet website).

According to some embodiments of the present invention, the technique to identify aspects of each subject can be obtained by using a voice spectral analysis (i.e., using human Bioacoustics test instead of the written test) that can be used to identify the strengths and weaknesses of the subject as well as the subject's personality type. Alternatively, such technique can also be used together with other physiologically test as described hereinbefore.

Human Bioacoustics refers to cross-disciplinary techniques that combines biology and acoustics. It includes voice spectral analysis that models the frequencies and architecture of human vocalizations to identify the innate mathematical templates found within the various system of the human body. These non-invasive techniques are being advanced to the extent that a computerized Vocal Profile, using a system of Frequency Equivalents, can be used to accurately quantify, organize, interpret, define, and extrapolate biometric information from the human voice. This information, in turn, provides the opportunity to obtain the four elements of the TAPE code.

The system of the present invention can be based on any suitable voice spectral analysis techniques. For example, such as the ones disclosed in "OpenEAR—Introducing the Munich open-source emotion and affect recognition toolkit", by F. Eyben, et al., pages 1-6, Affective Computing and Intelligent Interaction and Workshops, 2009. ACII 2009. 3rd International Conference on, in the "Speech emotion recognition based on HMM and SVM" by Yi-Lin Lin et al., vol. 8, pages 4898-4901, Machine Learning and Cybernetics, 2005. Proceedings of 2005 International Conference on, in the "Recognition of hesitations in spontaneous speech" by D. O'Shaughnessy, vol. 1, pages 521-524, Acoustics, Speech, and Signal Processing, 1992, ICASSP-92, 1992 IEEE International Conference on.

The voice spectral analysis can be done over telephone lines and with standard commercially available microphones. Based on such technologies and capabilities, the aforementioned "closing" between a client and an agent can be performed via a telephone conversation as the client's voice parameters can be analyzed over a telephone line.

The following Table (3) shows an example for setting the TAPE elements according to several voice characteristics of a person:

TABLE 3

| voice characteristics | T | A | P | E |
|---|---|---|---|---|
| Speech Intensity | 4 | 2 | 3 | 1 |
| Speech Pace | 2 | 4 | 3 | 1 |
| Speech Tone Recognition | 4 | 1 | 3 | 2 |
| Speech Monotony Recognition | 1 | 4 | 3 | 2 |
| Speech Mobility Recognition | 4 | 1 | 2 | 3 |
| Hyper Speaker Enthusiasm Recognition | 4 | 1 | 2 | 3 |
| The fastest waiting time for a response form the subject | 4 | 1 | 3 | 2 |
| Speaker Hesitation recognition | 2 | 3 | 1 | 4 |
| First sentence spoken in determination manner | 2 | 3 | 4 | 1 |
| Interference while the person on the other side (of the phone) still talking | 4 | 1 | 3 | 2 |

For example, in the table 3 the T, A, P and E values are set from 1 (which represents the higher voice related value) to 4 (which represents the lower voice related value).

The following Table (4) shows an example for words/sentences categorized according to the personality code:

TABLE 4

| Character | T | A | P | E |
|---|---|---|---|---|
| Manner of speech | Quite, listen, give facts, secure | Excitement, speak rapidly, give possibilities/options | Examples, stories, empathy | Short, focused, "to the point" |
| Targeted words for strengthening the profit (Pr) | Safe, harmony | Great deal, freedom, success | Pleasure, attractions for kids, joy, happiness, family | Exclusive, reputation |
| Targeted words for encouraging the imagination (Im) | Most secure, trusted deal | Profitable deal | A deal that involve family fun | Meets the requirement and proposes |

While some embodiments of the invention have been described by way of illustration, it will be apparent that the invention can be carried into practice with many modifications, variations and adaptations, and with the use of numerous equivalents or alternative solutions that are within the scope of persons skilled in the art, without departing from the spirit of the invention or exceeding the scope of the claims.

The invention claimed is:

1. A computer-implemented method for treating an individual to bring the individual to a higher level of consciousness (LOC) based on detecting a personality consciousness code and measuring a personal level of consciousness of the individual by analyzing a voice of the individual, comprising:
   a. generating and storing, in a database, reference voice characteristics of different persons that represent acoustic information expressed by human voice in a form of a time to frequency component relation, wherein said acoustic information is indicative of a dominant element, three main energy routes and extraversion-introversion personality traits;
   b. analyzing the acoustic information of the reference voice characteristics with a support vector machine to classify the acoustic information of the reference voice characteristics into 12 different personality consciousness codes, based on a determination that each personality code includes the dominant element, a balancing element, a transformational element, an energy route and a personality trait;
   c. capturing sound energy generated by the voice of said individual and producing an electronic representation of said sound energy in the form of a time to frequency component relation;
   d. performing a spectral analysis of the electronic representation of the sound to detect voice characteristics of the individual used to define a personality consciousness code for the individual, wherein the spectral analysis includes octaves analysis for detecting a coherence level between the 12 notes of an octave, wherein the coherence level between the notes reflects the level of balance of the personality consciousness code;
   e. comparing the voice characteristics of the individual with the reference voice characteristics with use of the support vector machine to determine the personality consciousness code of said individual and using the obtained voice characteristics of the individual to determine the level of consciousness (LOC) of the individual;
   f. treating the individual by transmitting a tone to the individual based on the detected coherence level between the 12 notes of said octave for balancing the personality consciousness code of said individual to bring the individual to a higher LOC or to an increased state-of-mind, thereby enabling said individual to better handle stressful situations, diseases or to improve decision making processes.

2. The method according to claim 1, wherein the dominant element is determined by applying spectral analysis to the sound energy generated by the individual voice, in order to extract speech intensity, speech pace, tone recognition and the coherence between the 12 notes on an octave scale.

3. The method according to claim 1, wherein the extraversion-introversion personality trait is determined by applying spectral analysis to the sound energy generated by the individual voice, in order to extract pitch levels and speech mobility and the coherence between the 12 notes on an octave scale, where high values of pitch and speech mobility indicate extroverted personality and low values of pitch and speech mobility indicate introverted personality.

4. The method according to claim 1, wherein the relation between said personality code elements is such that a relatively slight change in the transformational element will result in the largest change in the dominant and the balancing elements, thereby allowing the individual to move up from a lower level of consciousness (TAPE-S) to a higher level of consciousness (TAPE-O) with minimum effort.

5. The method according to claim 1, wherein a balanced personality code that defines an increased state-of-mind is obtained when a ratio between the three elements is determined as follows: the dominant element reflects 50% of the personality of the individual, the balancing element reflects 30% and the transformational element reflects 20%.

6. The method according to claim 1, wherein said tone includes a missing or negligible tone identified in said spectral analysis.

7. The method according to claim 1, wherein the individual is matched with an agent having the same dominant personality; and wherein, as the individual interacts with said agent, identifying at least one of the following four elements: a motivation element (Mo), a correlation element (Fr), an imagination element (Im), and a profit element (Pr), wherein all of said four elements are directly related to each other, and a function of said four elements enhances a chance of succeeding with closing a deal.

8. The method according to claim 1, further comprising identifying an element which drives or motivates the individual to perform an action, wherein said element is derived from the dominant element of said individual.

9. The method according to claim 1, further comprising continuously measuring the LOC of the individual during a conversation between the individual and another person and allowing said another person to identify the current LOC of said individual, in order to provide content that balances the personality consciousness code of said individual, and thus improving in real time an ability to close a deal between said individual and said another person.

10. The method according to claim 1, further comprising: continuously measuring, as said individual interacts with another person, the LOC of the other person and correlating a coherence of tones on an octave scale between the personality consciousness codes of the individual and said another person.

11. The method according to claim 1, wherein the personality consciousness code is determined by four roots elements T, A, P and E, that are presented on a consciousness scale, wherein one of said four elements, determines the dominate element, one determined the balancing element and one determines the transformational element, wherein the relations between the dominate element, the balancing element and the transformational element is such that a relatively slight change in the transformational element will result in the largest change in the dominant and the balancing elements, thereby allowing the individual to move up from a current LOC to a higher LOC with minimum effort, wherein the ratio between said elements is determined as follows: the dominate element reflects 50% of the individual personally code, the balancing element reflects 30% and the transformational element reflects 20%.

12. The method according to claim 1, further comprising measuring the consciousness level of the individual including using a set of questions, by performing the steps of:
   a. measuring an energy field of the individual by one or more sensing units while said individual gives answers to said set of questions, wherein said measured energy field represents an objective feedback of said individual while a content of the answers represents a subjective response of said individual;
   b. detecting the dominant element of said individual from said measured energy field and accordingly detecting the personality code; and
   c. comparing the subjective response of said individual (TAPE-S) with the measured objective feedback of said individual (TAPE-O) with respect to the detected personality code for determining the consciousness level of said individual, wherein while the difference between said subjective response and said measured objective response is relatively high, then the consciousness level of said individual is determined as relatively low on the consciousness scale, and vice versa.

13. The method of claim 1, where said treating further includes at least one selected therapy from the group consisting of psychological, alternative medicine, coaching and a vibrational therapy.

14. The method of claim 1, further comprising:
   g) adapting the treatment to a progress of the individual.

15. A non-transitory computer-readable medium having instructions stored thereon that are executable by a computing device to treat an individual to bring the individual to a higher level of consciousness (LOC) or to an increased state-of-mind by performing operations comprising:
   a) storing, in a database, reference voice characteristics of different persons that represent acoustic information as expressed by a human voice in a form of a time to frequency component relation, wherein said acoustic information is indicative of dominant elements, three energy routes and extraversion-introversion personality traits;
   b) classifying the acoustic information into 12 different personality consciousness codes, based on a determination that each personality code includes a dominant element, a balancing element, a transformational element, an energy route and a personality trait, by using a support vector machine that analyzes said acoustic information;
   c) receiving, by a computing system, data indicative of a sound energy generated by the voice of said individual;
   d) performing a spectral analysis of an electronic representation of the sound to detect voice characteristics of the individual used to define a personality consciousness code for the individual, wherein the spectral analysis includes octaves analysis for detecting a coherence level between the 12 notes of an octave, wherein the coherence level between the notes reflects a level of balance of the personality consciousness code;
   e) analyzing, by the computing system, said received sound energy to obtain voice characteristics from the electronic representation of said sound energy in the form of a time to frequency component relation;
   f) comparing said obtained voice characteristics with the reference voice characteristics and determining the personality consciousness code of said individual by using the support vector machine, and using the obtained voice characteristics to determine the level of consciousness (LOC) of the individual; and
   g) treating the individual by providing missing or negligible tones in the octave for balancing the personality consciousness code of said individual to bring the individual to a higher LOC or to an increased state-of-mind, thereby enabling said individual to better handle stressful situations, diseases or to improve decision making processes.

16. The non-transitory computer-readable medium of claim 15, wherein the operations further comprise generating feedback signals according to the transformational element to balance the personality consciousness code and to bring the individual to a higher LOC.

17. A system, for treating an individual to bring the individual to a higher level of consciousness (LOC) or to an increased state-of-mind comprising:
   i) one or more processors;
   ii) one or more memories having program instructions stored thereon that are executable by the one or more processors to cause the system to perform operations comprising:
      a) storing, in a database, reference voice characteristics of different persons that represent acoustic information as expressed by a voice of an individual in a form of a time to frequency component relation, wherein said acoustic information is indicative of dominant elements, three energy routes and extraversion-introversion personality;
      b) classifying the acoustic information into 12 different personality consciousness codes, based on a determination that each personality code includes a dominant element, a balancing element, a transformational element, an energy route and a personality trait, by using a support vector machine that analyzes said acoustic information;
      c) receiving, by a computing system, data indicative of a sound energy generated by the voice of said individual;
      d) performing a spectral analysis of an electronic representation of the sound to detect voice characteristics of the individual used to define a personality consciousness code for the individual, wherein the spectral analysis includes octaves analysis for detecting a coherence level between the 12 notes of an octave, wherein the coherence level between the notes reflects a level of balance of the personality consciousness code;
      e) performing, by the computing system, spectral analysis of said received sound energy in order to obtain voice characteristics from the electronic representation of said sound energy in the form of a time to frequency component relation; and f) comparing said obtained voice characteristics with the reference voice characteristics and determining the personality consciousness code of said individual by using the support vector machine, and using the obtained voice characteristics to determine a level of consciousness (LOC); and iii) a feedback unit adapted for treating the individual by providing missing or negligible tones in the octave for balancing the personality consciousness code of said individual to bring the individual to a higher LOC or to an increased state-of-mind, thereby enabling said individual to better handle stressful situations, diseases or to improve decision making processes.

18. The system according to claim 17, wherein said feedback unit is further adapted for providing content and/or transmitting acoustical signals to the individual according the transformational element resulting from calculated values of each element of the personality consciousness code, thereby enabling a balancing of the personality consciousness code of said individual.

* * * * *